United States Patent
Cohen et al.

(10) Patent No.: US 6,180,103 B1
(45) Date of Patent: Jan. 30, 2001

(54) PEPTIDE P277 ANALOGS, AND PHARMACEUTICAL COMPOSITIONS COMPRISING THEM FOR TREATMENT OR DIAGNOSIS OF DIABETES

(75) Inventors: Irun R. Cohen; Dana Elias; Matityahu Fridkin, all of Rehovot (IL)

(73) Assignee: Yeda Research and Development Co., Ltd., Rehovot (IL)

( * ) Notice: Under 35 U.S.C. 154(b), the term of this patent shall be extended for 0 days.

(21) Appl. No.: 08/860,300

(22) PCT Filed: Dec. 20, 1995

(86) PCT No.: PCT/US95/16596

§ 371 Date: Aug. 7, 1997

§ 102(e) Date: Aug. 7, 1997

(87) PCT Pub. No.: WO96/19236

PCT Pub. Date: Jun. 27, 1996

(30) Foreign Application Priority Data

Dec. 21, 1994 (IL) ......................................... 112094
Jul. 5, 1995 (IL) ......................................... 114460

(51) Int. Cl.$^7$ .......................... A61K 38/16; A61K 39/00; C07K 14/00; G01N 33/53

(52) U.S. Cl. .................................... 424/185.1; 424/184.1; 424/198.1; 514/13; 514/2; 514/885; 530/325; 435/7.1; 435/7.92; 435/975; 436/506; 436/518; 436/536; 436/543; 436/811

(58) Field of Search .............................. 424/184.1, 185.1, 424/198.1; 514/13, 2, 885; 530/325; 435/7.1, 7.92, 975; 436/506, 518, 536, 543, 811

(56) References Cited

U.S. PATENT DOCUMENTS 5,114,844    5/1992    Cohen et al. .................. 435/7.21

FOREIGN PATENT DOCUMENTS

90/10449  *  9/1990  (WO) .

OTHER PUBLICATIONS

A. Bendelac et al., "Syngeneic Transfer of Autoimmune Diabetes From Diabetic NOD Mice to Healthy Neonates", J. Exp. Med., vol. 166, pp. 823–832, Oct., 1987.

Mark A. Bowman et al., "Prevention of Diabetes in the NOD Mouse: Implications for Therapeutic Intervention in Human Disease", Immunology Today, vol. 15, No. 3, pp. 115–120, 1994.

Luis Castaño et al., "Type–I Diabetes: A Chronic Autoimmune Disease of Human, Mouse, and Rat", Annu. Rev. Immunol., vol. 8, pp. 647–679, 1990.

Dana Elias et al., "Induction and Therapy of Autoimmune Diabetes in the Non–Obese Diabetic (NOD/Lt) Mouse by a 65–kDa Heat Shock Protein", Proc. Natl. Acad. Sci. USA, vol. 87, pp. 1576–1580, Feb., 1990.

Dana Elias et al., "Autoimmune Diabetes Induced by the β–Cell Toxin STZ", Diabetes, vol. 43, pp. 992–998, Aug., 1994.

Daniel L. Kaufman et al., "Spontaneous Loss of T–Cell Tolerance to Glutamic Acid Decarboxylase in Murine Insulin–Dependent Diabetes", Nature, vol. 366, pp. 69–72, Nov. 4, 1993.

Arthur A. Like et al., "Streptozotocin–Induced Pancreatic Insulitis: New Model of Diabetes Mellitus", Science, vol. 193, pp. 415–417, Jul. 30, 1976.

T.R. Mosmann et al., "TH1 and TH2 Cells: Different Patterns of Lymphokine Secretion Lead to Different Functional Properties", Ann. Rev. Immunol., vol. 7, pp. 145–173, 1989.

Roland Tisch et al., "Immune Response To Glutamic Acid Decarboxylase Correlates With Insulitis in Non–Obese Diabetic Mice", Nature, vol. 366, pp. 72–75, Nov. 4, 1993.

Elias et al., "Peptide therapy for diabetes in nod mice.", The Lancet, vol. 343, pp. 704–706 (1994).

Elias et al., "Vaccination against autoimmune mouse diabetes with a T cell epitope of the human 65–kda heat shock protein.", Proc, Nat. Acad. Sci. USA, vol. 88, 3088–3091 (1991).

Funda et al. APMIS 106:1009–1016, Abstract thereof.*

* cited by examiner

*Primary Examiner*—Ronald B. Schwadron
(74) *Attorney, Agent, or Firm*—Browdy And NEimark

(57) ABSTRACT

A peptide having the structure of the p277 sequence of hsp60 in which one or both cysteine residues are replaced by valine residues and/or in which the Thr$^{19}$ residue is replaced by Lys, has substantially the same biological activity as p277 but with substantially improved stability. The novel p277 analogues may be used for every purpose that p277 can be used.

26 Claims, 4 Drawing Sheets

PEPTIDE P277 ANALOGS, AND PHARMACEUTICAL COMPOSITIONS COMPRISING THEM FOR TREATMENT OR DIAGNOSIS OF DIABETES

FIELD OF THE INVENTION

The present invention relates to novel peptides being variants of an epitope of the human 60 kDa heat shock protein (hsp 60) and to pharmaceutical compositions comprising them and methods for the diagnosis and treatment of insulin-dependent diabetes mellitus (IDDM) using such peptides.

BACKGROUND OF THE INVENTION

Type I diabetes, or IDDM, is an autoimmune disease caused by T cells that attack and destroy the insulin producing β-cells located in the islets of the pancreas (Castano and Eisenbarth, 1990). The autoimmune process culminating in IDDM begins and progresses without symptoms. The disease surfaces clinically only when the cumulative loss of β-cells exceeds the capacity of the residual β-cells to supply insulin. Indeed, the collapse of glucose homeostasis and clinical IDDM is thought to occur only after 80–90% of the β-cells have been inactivated by the immune system. Thus, patients who can be identified as suffering from IDDM are bound to be in an advanced stage of autoimmune destruction of their β-cells. Moreover, diagnosis of incipient, preclinical diabetes by the detection of immunological markers of β-cell autoimmunity can be made only after the onset of the autoimmune process. Therefore, the therapeutic quest is to find a safe, specific and effective way to turn off an autoimmune process that is already well underway.

The present inventors have examined this question before by studying the spontaneous diabetes developing in mice of the NOD strain, which is considered to be a faithful model of human IDDM (Castano and Eisenbarth, 1990). NOD mice develop insulitis around 4 weeks of age, which begins as a mild peri-islet infiltrate and progresses to severe intra-islet inflammation. Hyperglycemia, which attests to insulin insufficiency, begins in the females in our colony at about 14–17 weeks of age. By 35–40 weeks of age, almost all the female NOD mice have developed severe diabetes and most die in the absence of insulin treatment. Male NOD mice have a lower incidence of disease, for reasons that are not clear. The diabetes of NOD mice has been shown to be caused by autoimmune T cells (Bendelac et al., 1987).

T cell reactivity and autoantibodies to various antigens have been detected in human IDDM patients as well as in NOD mice (Elias, 1994), and it is not clear whether immunity to any single one of the possible target antigens is the primary cause of the disease. Beyond the question of causation is the question of therapy.

It has been demonstrated that the initiation of the autoimmune process in NOD mice can be prevented by subjecting the mice, before the onset of diabetes, to various manipulations such as restricted diet, viral infections, or non-specific stimulation of the immune system (Bowman et al., 1994). NOD diabetes is also preventable by induction of immunological tolerance in pre-diabetic mice to the antigen glutamic acid decarboxylase (GAD) (Kaufman et al., 1993; Tisch et al., 1993).

The present inventors have found previously that the diabetes of NOD mice can be prevented by T cell vaccination using T cells specific for the p277 peptide sequence of the human hsp60 molecule (Elias et al., 1991). This protein was formerly designated hsp65, but is now designated hsp60 in view of more accurate molecular weight information; by either designation, the proteins are the same.

The p277 peptide, being the epitope of the human hsp60 involved in IDDM and corresponding to positions 437–460 of the human hsp60 sequence, was first described in Israeli Patent Application No. 94241 of the present applicant and in Elias and Cohen, 1994, and has the following sequence:

Val-Leu-Gly-Gly-Gly-Cys-Ala-Leu-Leu-Arg-Cys-Ile-Pro-Ala-Leu-Asp-Ser-Leu-Thr-Pro-Ala-Asn-Glu-Asp (SEQ ID NO:1)

Administration of the p277 peptide itself at the onset of insulitis was shown also to prevent the development of diabetes, probably by down-regulating the anti-p277 immunity that is essential for NOD diabetes (Elias et al., 1991; Israeli Patent Application No. 94241). Recent studies have indicated that the p277 peptide may also be used to reverse β-cell autoimmunity that has progressed to an advanced stage (Elias and Cohen, 1994).

The laboratory of the present inventors has recently reported that a form of autoimmune diabetes can be induced in the C57BL/KsJ strain of mice by the administration of a very low dose of the β-cell toxin streptozotocin (STZ) (Elias et al., 1994). Whereas the standard low dose of STZ of 40 mg/kg administered daily for 5 days usually induces clinical diabetes within 3 weeks, the administration of 30 mg/kg for 5 days induces clinical diabetes only after a lag period of about 3 months. This model of induced diabetes is marked by the appearance in the prodrome period of autoantibodies to insulin, anti-idiotypic antibodies to the insulin autoantibodies, and autoantibodies to hsp60. The mice also manifest spontaneous T-cell reactivity to hsp60 and to its p277 peptide (Elias et al., 1994). Thus, the lower than standard low dose of STZ appears to trigger an autoimmune process not unlike that observed in the spontaneous diabetes developing in NOD mice (Elias et al., 1990).

It is an object of the present invention to provide variants of peptide p277, such variants being useful for the diagnosis and treatment of IDDM.

SUMMARY OF THE INVENTION

In a study of fragments and variants of the peptide p277, it was unexpectedly found that the peptides in which the sole threonine residue was replaced by a lysine residue and/or one or both of the cysteine residues were replaced by valine residue(s), were as active as p277 in the treatment of diabetes. These results were even more surprising since the substitution of the cysteine residues by serine residues resulted in inactive peptides.

The present invention thus relates to a peptide comprising the sequence I:

(SEQ ID NO:2)

$$\text{Val-Leu-Gly-Gly-Gly-}X_1\text{-Ala-Leu-Leu-Arg-}X_2\text{-}$$
$$\overset{6}{\phantom{Val}}\phantom{-Leu-Gly-Gly-Gly-}\overset{11}{\phantom{X_1}}$$

$$\text{Ile-Pro-Ala-Leu-Asp-Ser-Leu-}X_3\text{-Pro-Ala-Asn-Glu-Asp}$$
$$\overset{19}{\phantom{Ile-Pro-Ala-Leu-Asp-Ser-Leu-}}$$
(I)

wherein $X_1$ and $X_2$ each is a Cys or Val residue and $X_3$ is a Thr or Lys residue, but $X_1$ and $X_2$ cannot both be Cys residues when $X_3$ is a Thr residue.

In specific embodiments of the invention, the peptide consists of the sequence I wherein both $X_1$ and $X_2$ are Cys and $X_3$ is Lys, herein p277(Lys$^{19}$) (SEQ ID NO:3) or $X_1$ is Val, $X_2$ is Cys and $X_3$ is Thr or Lys, herein p277(Val$^6$) (SEQ ID NO:4) and p277(Val⁶-Lys¹⁹) (SEQ ID NO:5), respectively; or X₁ is Cys, X₂ is Val and X₃ is Thr or Lys, herein p277(Val¹¹) (SEQ ID NO:6) and p277(Val¹¹-Lys¹⁹) (SEQ ID NO:7), respectively; or both X₁ and X₂ are Val and X₃ is Thr or Lys, herein p277(Val⁶-Val¹¹) (SEQ ID NO:8) and p277 (Val⁶, ¹¹-Lys¹⁹) (SEQ ID NO:9), respectively. The p277 (Val⁶-Val¹¹) peptide is also referred to herein as p277(V).

It is further an object of the present invention to provide methods and kits for the early diagnosis of IDDM using a peptide of sequence I of the invention. In the course of developing IDDM, animals express hsp60 molecules, or molecules which are cross-reactive therewith, which find their way into the blood and urine of the animals. They also express antibodies and T cells directed specifically to such molecules. Thus, the presence of hsp60 (or molecules which are cross-reactive therewith) or antibodies or T cells specific thereto in blood or urine, serves as an assay for the detection of the IDDM process before the destruction of beta cells is completed and the individual is doomed to life-long diabetes.

The presence or incipience of IDDM in a patient can be diagnosed by testing the blood or urine of said patient for the presence of anti-hsp60 antibodies or T cells which are immunologically reactive with human hsp60, using as antigen a peptide of sequence I of the invention. Indeed, any of the procedures previously described as being operable using peptide p277, such as those described in PCT International Application published under No. WO 90/10449, hereby incorporated herein by reference, can also be used substituting for p277 a peptide of sequence I of the present invention.

Accordingly, the present invention provides a method for diagnosing the presence or incipience of IDDM in a patient, comprising testing said patient for the presence of anti-hsp60 antibodies or of a T cell which immunoreacts with hsp60, whereby a result indicating the positive presence of anti-hsp60 antibodies, of a T cell which immunoreacts with hsp60, or a T cell or of a T cell which immunoreacts with hsp60, indicates a high probability of the presence or incipience of IDDM.

In the method for diagnosing IDDM, the patient may be tested for the presence of anti-hsp60 antibodies, wherein said test method may comprise a radioimmunoassay or an ELISA test.

The patient may also be tested for the presence of a T cell which immunoreacts with hsp60. In one embodiment of this aspect, the test method comprises a T cell proliferation test comprising the steps:

(i) preparing a mononuclear cell fraction containing T cells from a blood sample obtained from said patient;

(ii) adding to said mononuclear cell fraction an antigen selected from a peptide of sequence I of the invention;

(iii) incubating said cell fraction in the presence of said antigen for a suitable period of time and under suitable culture conditions;

(iv) adding a labeled nucleotide to the incubated cell culture of (iii) at a suitable time before the end of said incubation period to provide for the incorporation of said labeled nucleotide into the DNA of proliferating T cells; and (v) determining the amount of proliferating T cells by analysis of the amount of labeled nucleotide incorporated into said T cells.

In step (iv), above, said labeled nucleotide is preferably ³H-thymidine. The determination of the amount of proliferating T cells is made by calculation of the stimulation index of the T cells by standard methods.

In another embodiment of this aspect of the invention, the test method comprises a T-cell cytokine response test, in which steps (i) to (iii) are as in the above T cell proliferation test, and in a fourth step (iv) the presence of cytokine, such as IFN-γ, IL-2, IL-4, IL-6, IL-10, TNFα or TGFβ, secreted by the responding lymphocytes into the medium, is detected by standard methods with commercially available kits.

In another aspect, the invention provides an in vivo method wherein an antigen selected from a peptide of sequence I is injected subcutaneously into a patient and the occurrence of a detectable skin reaction (DTH) is observed.

The present invention also relates to means for performing such assays, as well as kits for performing such assays. The kits may be prepared for carrying out any of the various assays used for accomplishing the present invention. Each such kit includes all of the materials necessary to conduct a single assay or a fixed number of assays. For example, such a kit for determining the presence of anti-hsp60 antibodies may contain a solid-phase immobilized peptide of sequence I and a tagged antibody capable of recognizing the non-variable region of the anti-hsp60 antibody to be detected, such as tagged anti-human Fab. The kit may also contain directions for using the kit and containers to hold the materials of the kit. Any conventional tag or label may be used, such as a radioisotope, an enzyme, a chromophore or a fluorophore. A typical radioisotope is iodine-125 or sulfur-35. Typical enzymes for this purpose include horseradish peroxidase, β-galactosidase and alkaline phosphatase.

A kit for diagnosing the presence of IDDM by testing for the presence of anti-hsp60 antibodies comprises:

(i) an antigen selected from a peptide of sequence I; and (ii) a tagged antibody capable of recognizing the non-variable region of said anti-hsp60 antibodies to be detected.

A kit for diagnosing the presence of IDDM by testing for the presence of a T cell which immunoreacts with hsp60 comprises:

(i) an antigen selected from a peptide of sequence I;

(ii) a suitable medium for culture of lymphocytes (T cells); and (iii) either a labeled nucleotide for the T cell proliferation test, or a cytokine, e.g., IFN-γ, IL-2, IL-4, IL-6, IL-10, TNFα or TGFβ, assay kit, for the cytokine test.

For the in vivo test, the kit will comprise only a peptide of sequence I in a suitable form for injection.

The present invention further relates to means for preventing or treating IDDM. Vaccination with the antigen peptide of sequence I of the present invention can provide a specific down regulation of autoimmunity to the antigen, and effectively creates a resistance to the autoimmune process of IDDM. The same is true with respect to vaccination with T cells specific to such antigens, in attenuated or avirulent form or after having been treated to improve their antigenicity, or fragments or active fractions thereof. If the patient is shown to already be in the pre-clinical incipient stages of IDDM, injection with such an antigen or T cell (or fraction) can create a down regulation of autoimmunity for this antigen and thus arrest the autoimmune process before significant, permanent damage is done. The peptide can also be used as a therapeutic agent to arrest the autoimmune-process even after it is far advanced, as shown recently by the inventors of the present invention regarding the treatment of NOD mice with the peptide p277 (Elias and Cohen, 1994).

Accordingly, the present invention provides a preparation for preventing or treating insulin-dependent diabetes mellitus (IDDM), comprising a T cell product selected from the group consisting of: (a) human T cells which manifest specificity for the p277 sequence of human hsp60, which cells have been activated by incubating in the presence of said peptide of sequence I; (b) said human T cells of (a)

which have been irradiated or otherwise attenuated; (c) said human T cells of (a) which have been subjected to pressure treatment by means of hydrostatic pressure, treatment with a chemical cross-linking agent and/or treatment with a cytoskeletal cross-linking agent; (d) fragments of, or surface proteins shed from, the T cells of (a), (b) or (c); or (e) a peptide consisting essentially of the variable region of the receptor of (a) specific for said protein, or a salt, functional derivative, precursor or active fraction thereof.

In a preferred embodiment of the invention, the preparation comprises autologous human T cells obtained from the IDDM patient to be treated, which T cells have been activated by in vitro contact with said peptide of sequence I. Such specific and activated T cells are then administered to the same patient from whom they were originally obtained.

The present invention also provides a pharmaceutical composition for the prevention or treatment of IDDM comprising a pharmaceutically acceptable carrier and, as active principle, an effective amount of a peptide of sequence I, a salt or a functional derivative thereof. The pharmaceutically acceptable carrier is preferably an oil vehicle such as an emulsion of mineral oil known as incomplete Freund's adjuvant (IFA). However, IFA, as well as complete Freund's adjuvant (CFA; a preparation of mineral oil containing various amounts of killed organisms of Mycobacterium) are not allowed for human use because the mineral oil is not metabolizable and cannot be degraded by the body.

It has now been found by the present inventors that certain fat emulsions, which have been in use for many years for intravenous nutrition of human patients, can also act as a vehicle for peptide therapy using the peptides of the present invention. Two examples of such emulsions are the available commercial fat emulsions known as Intralipid and Lipofundin. "Intralipid" is a registered trademark of Kabi Pharmacia, Sweden, for a fat emulsion for intravenous nutrition, described in US patent no. 3,169,094. "Lipofundin" is a registered trademark of B, Braun Melsungen, Germany. Both contain soybean oil as fat (100 or 200 g in 1,000 ml distilled water: 10% or 20%, respectively). Egg-yolk phospholipids are used as emulsifiers in Intralipid (12 g/l distilled water) and egg-yolk lecithin in Lipofundin (12 g/l distilled water). Isotonicity results from the addition of glycerol (25 g/l) both in Intralipid and Lipofundin.

The invention further relates to a method of preventing or treating IDDM which comprises administering to a patient in need thereof a pharmaceutical composition comprising a peptide of sequence I or a preparation comprising T cells which have developed specificity to said peptide of sequence I of the invention.

DETAILED DESCRIPTION OF THE INVENTION

Figure 1:
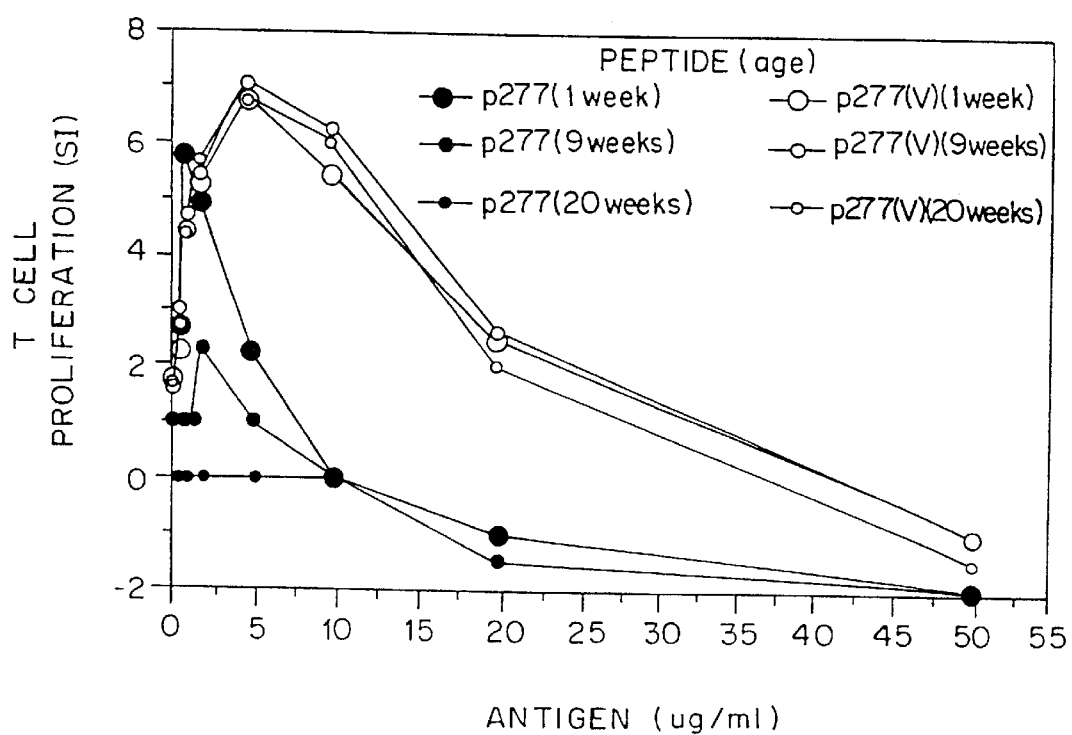
FIG. 1 is a graph showing the stability of p277 and p277(Val$^6$-Val$^{11}$). The closed circles designate results using p277 and the open circles p277 (Val$^6$-Val$^{11}$). The large circles represent results after 1 week of storage, the medium-size circles after 9 weeks, and the smallest circles after 20 weeks.

Whenever a "peptide of sequence I" is mentioned in the invention, also salts and functional derivatives thereof are contemplated, as long as the biological activity of the peptide with respect to diabetes is maintained.

"Salts" of the peptide I contemplated by the invention are physiologically acceptable organic and inorganic salts.

"Functional derivatives" of the peptide I as used herein covers derivatives which may be prepared from the functional groups which occur as side chains on the residues or the N- or C-terminal groups, by means known in the art, and are included in the invention as long as they remain pharmaceutically acceptable, i.e., they do not destroy the activity of the peptide insofar as its similarity to the known activity of p277 is concerned, do not confer toxic properties on compositions containing it and do not adversely affect the antigenic properties thereof. Such "functional derivatives" are not intended to comprehend such changes which effectively convert one amino acid to another.

Subject to the above qualifications, these derivatives may, for example, include aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups) or O-acyl derivatives of free hydroxyl group (for example that of seryl or threonyl residues) formed by reaction with acyl moieties.

The peptide of sequence I of the invention can be used as immunogen in pharmaceutical compositions, particularly vaccines for the alleviation and treatment of IDDM, as well as an antigen in diagnostic compositions for the diagnosis of IDDM. These pharmaceutical and diagnostic compositions, which may be prepared in a manner known in the art, also form part of the present invention.

When used for therapeutic treatment or as a prophylactic vaccine, the peptide of the present invention is preferably administered with a biologically active carrier which promotes the TH1→TH2 shift of the autoimmune T cells. T cells of the CD4 helper type are classified in two groups according to the cytokines they secrete when activated (Mosmann and Coffman, 1989): TH1 cells secrete IL-2 and IFN-γ, while TH2 cells secrete IL-4 and IL-10. Such a vehicle is preferably a fat emulsion comprising 10–20% triglycerides of plant and/or animal origin, 1.2–2.4% phospholipids of plant and/or animal origin, 2.25–4.5% osmoregulator, 0–0.5% anti-oxidant, and sterile water to 100%. Such vehicle is most preferably Intralipid or Lipofundin. Use of such vehicles is described in an Israeli patent application (identified by applicant's reference 9523) filed on even date with the date of filing of the Israeli application on the present invention (identified by applicant's reference 9451A), with the same applicant as the present application, the entire contents of which are hereby incorporated herein by reference.

The therapeutic composition in accordance with the present invention may be administered orally or parenterally, such as subcutaneously, intramuscularly, intravenously, intranasally or intrarectally.

The examples herein establish the effectiveness of therapeutic treatment with the compounds and compositions of the present invention in scientifically accepted animal models of human IDDM.

EXAMPLES

Materials and Methods (i) Mice. Inbred female mice of the NOD/Lt strain were supplied by the Animal Breeding Center of the Weizmann Institute of Science, Rehovot, Israel. These micef spontaneously develop autoimmune diabetes at 14 to 17 weeks of age that mimics IDDM in humans.

(ii) Peptides. Peptides were synthesized by standard Fmoc chemistry using an ABIMED synthesizer (FRG) and purified on HPLC by reverse phase chromatography. Sequences were confirmed by amino acid analysis. The following peptides were synthesized: the p277 peptide; the control peptide p278 of the sequence: Asn-Glu-Asp-Gln-Lys-Ile-Gly-Ile-Glu-Ile-Ile-Lys-Arg-Thr-Leu-Lys-Ile (SEQ ID NO:10), corresponding to positions 458–474 of the human hsp60 molecule; fragments of p277: the amino half of p277 (p277.N), the carboxy half of p277 (p277.C), and p277C combined with p278 (p277.C-p278); the peptide p277 (Lys$^{19}$); and peptide p277 with various amino acid substitutions for the two cysteine residues in the sequence as follows: p277 with bridged —SH groups (p277(bridged Cys—Cys)); p277 with both cysteine residues replaced by valine (p277(Val$^6$-Val$^{11}$)) or by serine (p277(Ser$^6$-Ser$^{11}$)).

(iii) Treatment and follow-us. Mice were treated with emulsions of p277, of the other peptides, or of bovine serum albumin (BSA, purchased from Sigma, St. Louis, Mo., USA) in volumes of 0.1 ml injected subcutaneously into the back. The antigens were diluted in PBS and emulsified in an equal volume of mineral oil (incomplete Freund's adjuvant (IFA); Sigma) or 10% Intralipid. The mice were tested for blood glucose levels at 10 A.M. in a non-fasting state as described (Elias et al., 1991) at the time of treatment (7, 12, 15, or 17 weeks of age) and, in those mice that survived, at the age of 40 weeks. Significant hyperglycemia was considered to be a glucose concentration of 11.1 mM/L or greater because this concentration of blood glucose was 3 standard deviations higher than the mean blood glucose concentration measured in 100 healthy mice (not shown). Histological examination of the islets of the pancreas was done on sections stained with hematoxylin and eosin. The sections were scored independently by two observers who both were unaware of the identity of the groups. The chi square test was used to ascertain the statistical differences between the various treatments.

(iv) T-cell proliferation assay. Cells of clone C9 and spleen-cell suspensions obtained from female NOD mice were assayed for T-cell proliferation as described previously (Elias et al., 1991). Briefly, $1\times10^5$ clone cells/ml or $1\times10^6$ splenocytes/ml were incubated in quadruplicate for 72 hr in 0.2 ml of culture medium in microtiter wells in the presence or absence of various antigens at 5 μg/ml. Proliferation was measured by the incorporation of [$^3$H]-thymidine into DNA during the final 12 hr of incubation. The results were computed as the stimulation index: the ratio of the mean test cpm in the presence of antigen to the mean background cpm in the absence of antigen. Standard deviations between quadruplicates were always <10% of the mean cpm. The background was <1000 cpm in splenocyte experiments and <200 cpm with C9 cells. The spleen of each mouse was tested separately. Results of each group of mice are shown as the mean ±SD.

EXAMPLE 1
Treatment of NOD mice with p277 or fragments thereof

To test whether either of the two 12-amino acid halves of the p277 peptide, alone or combined, are effective in NOD mice as is p277, female NOD mice were treated at the age of 7 weeks by subcutaneous inoculation of 50 μg of various peptides in oil. The status of the mice by 40 weeks of age was determined.

The results are shown in Table 1. It can be seen that the control hsp60 peptide p278 had no effect on development of disease: of the 40 mice treated, all were diabetic and 90% were dead by 40 weeks of age. In contrast, the p277 peptide completely prevented death and cured 60! of the 20 treated mice. The fragments of p277 were less effective: the amino half of p277 (p277.N), the carboxy half of p277 (p277.C) and a mixture of both (p277.N, p277.C) worked about half as well as did the intact p277. Peptide p277.C was synthesized attached to peptide p278 to produce a longer peptide; however, p277.C-p278 was not any better than p277.C. alone. Therefore, it can be concluded that the full therapeutic effect requires the intact p277 peptide.

TABLE 1

Treatment of NOD Mice with p277 or its Fragments Status at 40 Weeks Diabetes

| Peptide treatment (50 μg) | Number of mice | Healthy % | Hyperglycemic % | Death % |
|---|---|---|---|---|
| p278 | 40 | 0 | 100 | 90 |
| p277 | 20 | 60* | 40 | 0* |
| p277.N | 20 | 20 | 80 | 50* |
| p277.C | 20 | 30 | 70 | 40* |
| p277.N, p277.C | 20 | 35* | 65 | 40* |
| p277.C-p278 | 20 | 25 | 75 | 50* |

*p < 0.01 compared to the group treated with control peptide p278.

EXAMPLE 2
Treatment of NOD mice with p277 substitution peptides

The following peptides were tested in NOD mice: p277, p277(bridged Cys—Cys), p277(Val$^6$-Val$^{11}$) and p277(Ser$^6$-Ser$^{11}$).

NOD females were treated with 100 μg of peptide in a-0.2 cc emulsion of mineral oil (IFA) administered subcutaneously. Mice were treated at 12 weeks of age and the incidence of diabetes was performed at 30 weeks.

As shown in Table 2, p277(Val$^6$-Val$^{11}$) was as effective as p277 in treatment of diabetes, the incidence of diabetes in untreated mice being 80%, while p277 and p277(Val$^6$-Val$^{11}$) treated mice show an incidence of 22% and 23%, respectively. On the other hand, neither p277(bridged Cys—Cys) nor p277(Ser$^6$-Ser$^{11}$) had any therapeutic effect. Two additional variants of p277, in which the cysteine residues at position 6 and 11 were replaced by alanine or 7-aminobutyric acid residues, were also not effective when tested in vitro both on the clone C9 cells and on NOD splenic T-cells. As these two peptides were not recognized by anti-p277 specific T cells (not shown), they were not further tested in vivo for therapeutic effect.

TABLE 2

Treatment of NOD mice with p277 substitutions

| Peptide treatment | Incidence of diabetes (%) | Number of Recipients |
|---|---|---|
| none | 80 | 100 |
| p277 | 22* | 200 |
| p277 (bridged Cys—Cys) | 70¶ | 10 |
| p277 (Val$^6$-Val$^{11}$) | 23* | 52 |
| p277 (Ser$^6$-Ser$^{11}$) | 85¶ | 20 |

*p < 0.01 compared to incidence of diabetes in mice treated with adjuvant alone.
¶No significant difference compared to incidence of diabetes in mice treated with adjuvant alone.

EXAMPLE 3
Stability of p277(Val$^6$-Val$^{11}$)

Since the reason for replacing the cysteines was the problematic stability of the p277 peptide, the stability of the p277(Val$^6$-Val$^{11}$) was tested at several time points after its synthesis. The p277 peptide is unstable and deteriorates even under strict conditions (lyophilized powder in vacuum, −20° C.).

In order to compare the stability of p277 with its p277 (Val$^6$-Val$^{11}$) analog, both peptides were synthesized at the same time and stored as dry powder at −20° C. At 1, 9 and 20 weeks after the date of synthesis, an aliquot was weighed, dissolved and tested. The readout for the stability of the peptide was its ability to stimulate the T cell clone C9.

FIG. 1 demonstrates the results of the experiment. It can be seen that, while the native p277 lost most of its effect within 9 weeks and all of it by 20 weeks after synthesis, p277(Val$^6$-Val$^{11}$) was unchanged after 20 weeks of storage.

As it is believed that the instability of p277 is caused by the cysteine residues, it is expected that any of the analogs of the present invention which retain the biological activity of p277 will have an improved stability over p277 in a manner similar to that demonstrated in this example for p277(Val$^6$-Val$^{11}$).

EXAMPLE 4

Treatment of NOD female mice with p277 or p277(Val$^6$-Val$^{11}$) reverses insulitis NOD female mice were treated at 12 weeks of age with 100 μg/mouse of unmodified p277 or p277(Val$^6$-Val$^{11}$) in 0.1 cc emulsion of mineral oil (incomplete Freund's adjuvant), subcutaneously. Control mice received an emulsion of PBS and mineral oil. At 6 months of age, 5 mice of each group were sacrificed, their pancreas removed and fixed in bouin and sections were stained by hematoxylin-:eosin. The insulitis was scored in a blind fashion. Since the control mice developed severe diabetes, they were sacrificed at 5 months of age. By then, the control mice blood glucose levels were in the range of 29–48 mmol/L. The results are shown in Table 3.

TABLE 3

Treatment of NOD female mice with p277 or p277 (Val$^6$–Val$^{11}$) reverses insulitis

| Peptide treatment (12 weeks) | number of islets | Histologic Examination (22 weeks) | | |
|---|---|---|---|---|
| | | clear % | Insulitis peri-islet % | intra-islet % |
| None | 83 | 10 | 23 | 67 |
| p277 | 49 | 25 | 69 | 6 |
| p277 (Val$^6$–Val$^{11}$) | 62 | 52 | 31 | 17 |

At 12 weeks of age, the time of treatment, about 60!% of the islets in the untreated mice showed intra-islet insulitis, about 20% of the islets had peri-islet insulitis, and about 20% of the islets showed no insulitis. Intra-islet infiltration is considered to be a severe form of insulitis associated with lack of β-cell function. As shown in Table 3, a marked divergence in the appearance of the islets developed in the two treated groups compared to control mice treated with the oil alone. The mice treated with the oil (control) showed a progressive fall in the proportion of unaffected islets and only 10% normal islets could be seen by 22 weeks of age, a time when all of the mice were overtly diabetic. About 67% of the islets showed intra-islet insulitis at 22 weeks and the remaining 23% of the islets showed peri-islet insulitis. In contrast, the mice treated with p277 or with p277(Val$^6$-Val$^{11}$) showed a rise in the numbers of normal islets (between 25% and 52%) and a fall in the number of islets with intra-islet insulitis (between 6% and 17%). The islets with peri-islet insulitis rose to about. 31%-69%. Thus, p277 and p277(Val$^6$-Val$^{11}$) treatments were associated with an improved histological picture consistent with reversal of the degree of insulitis persisting for over 3 months after treatment.

Additional results using p277 (v) in female NOD mice.

Fifteen additional experiments have been done in which groups of 10 NOD female mice each were treated with p277(V) in oil or with oil alone at the ages of 12–15 weeks. Of the total of 150 mice treated with oil alone, 90% developed diabetes and 85% died by the age of 32 weeks. In contrast, the p277(V) treated mice showed an incidence of diabetes of only 50% (p<0.01) and only 20% died of severe disease (p<0.01). Therefore, late treatment with p277(V) was effective in arresting the development of lethal diabetes.

EXAMPLE 5

Peptide therapy of type I diabetes using p277(Val$^6$-Val$^{11}$) in lipid emulsions Autoimmune destruction of the insulin-producing β-cells in the pancreas is mediated by T-lymphocytes. An inflammatory infiltrate develops around the pancreatic islets at 5–8 weeks of age and β-cell destruction leading to insulin deficiency and overt diabetes becomes manifested at: 14–20 weeks of age affecting almost 100% of female NOD mice by 35–40 weeks of age.

NOD female mice were treated with 100 μg of peptide p277(Val$^6$-Val$^{11}$) per mouse subcutaneously in 0.1 ml of PBS or of a 10% lipid emulsion composed of 10% soybean oil, 1.2% egg phospholipids and 2.25% glycerol (Intralipid, Kabi Pharmacia AB, Sweden).

The incidence of diabetes at 6 months of age and the production of anti-p277(Val$^6$-Val$^{11}$) antibodies was followed. Diabetes was diagnosed as persistent hyperglycemia, blood glucose levels over 11.1 mmol/L measured at least twice at weekly intervals with Beckman Glucose Analyzer II. Successful peptide treatment was assayed by maintenance of a normal blood glucose concentration (less than 11.1 mmol/L), remission of the intra-islet inflammation of the pancreatic islets (insulitis) and induction of antibodies to the therapeutic peptide as an indicator of a TH2-type immune response. The results are shown in Table 4.

TABLE 4

Incidence of Diabetes at 6 months

| Treatment | Diabetes Incidence (%) | Death (%) |
|---|---|---|
| p277 (Val$^6$–Val$^{11}$)/PBS | 90 | 80 |
| p277 (Val$^6$–Val$^{11}$)/Intralipid | 45* | 20* |
| none | 100 | 90 |

*p < 0.01 compared to untreated NOD mice

As can be seen from Table 4, treatment with a peptide of the present invention administered in Intralipid was effective in reducing the incidence of diabetes and death.

On the other hand, treatment administered in PBS was ineffective.

EXAMPLE 6

Peptides p277 and p277(Val$^6$-Val$^1$) are immunologically cross-reactive

Figure 2:
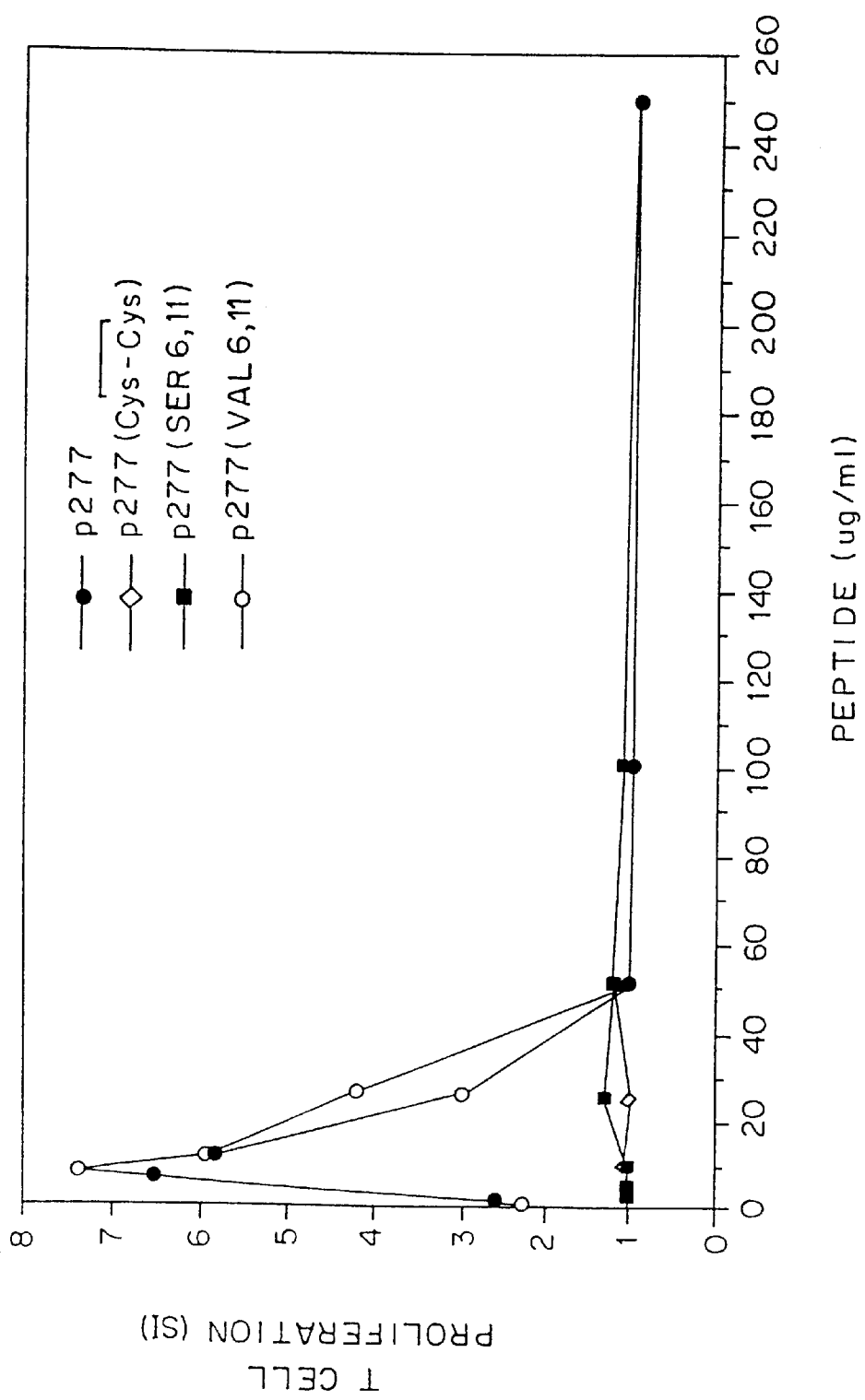
FIG. 2 shows that NOD T cells of the diabetogenic clone C9 proliferate in response to the peptides p277 (closed circles) and p277(Val$^6$-Val$^{11}$) (open circles).

Cells of the T-cell clone C9 isolated from prediabetic NOD mice were incubated with peptides p277 (closed circles), p277(Val$^6$-Val$^{11}$) (open circles), p277(Ser$^6$-Ser$^{11}$) (closed squares) and p277(bridged Cys—Cys) (open lozenges). The results are shown in FIG. 2. The clone C9 was found to manifest a positive proliferation response only to peptides p277 and p277(Val$^6$-Val$^{11}$). This proves that p277 and p277(Val$^6$-Val$^{11}$) are cross-reactive and that the peptides p277(Ser$^6$-Ser$^{11}$) and p277(bridged Cys—Cys), which are not effective therapeutically, are not immunologically cross-reactive.

EXAMPLE 7

Newly diagnosed IDDM patients show T-cell proliferative responses to both D277 and p277(Val$^6$-Val$^{11}$)

Newly diagnosed (2–4 weeks) IDDM patients were tested in a proliferation assay. Peripheral blood lymphocytes were isolated from whole heparinized blood on ficol-hypaque, and screened in vitro for proliferation, measured as $^3$H-thymidine incorporation, induced by hsp60 peptides p277, p277(Val$^6$-Val$^{13}$) and control peptide p278. The T cell proliferative response is depicted as stimulation index (SI): the ratio between peptide-stimulated thymidine incorporation and background (no antigen added) thymidine incorporation by the T cells.

TABLE 5

Newly diagnosed IDDM patients show T-cell proliferative responses to both p227 and p227 (Val$^6$–Val$^{11}$)

| | T cell proliferation (SI) | | |
|---|---|---|---|
| Patient | p227 | p227 (Val6–Val11) | p278 |
| IDDM#68 | 3.5 | 3.2 | 0.8 |
| IDDM#69 | 2.5 | 5.0 | 0.5 |

As shown in Table 5, newly diagnosed IDDM patients respond to p277(Val$^6$-Val$^{11}$) as well as to the p277 peptide. Therefore, p277(Val$^6$-Val$^{11}$) is immunologically equivalent to p277. Since the therapeutic effect of p277 is mediated by immunological recognition, the fact that p277(Val$^6$-Val$^{11}$) is immunologically cross-reactive with p277, indicates it can be used instead of p277 in treating diabetes.

EXAMPLE 8

T-cell responses to hsp60 and peptide in IDDM and healthy individuals

Twenty one IDDM patients and fourteen healthy blood-donors were screened for anti-hsp60 and p277(V) by means of the proliferation assay of Example 7. Tables 6 and 7 show the proliferative T cell response (stimulation index; SI) of each individual to control antigen (control Ag), i.e., tetanus toxoid and influenza virus—Texas strain, to whole recombinant hsp60 and to p277(V). SI values of 3 or greater were considered to be positive.

TABLE 6

Proliferative T cell response of IDDM patients

| | | | Time since | T-cell responses (stimulation index) to: | | |
|---|---|---|---|---|---|---|
| Patient | | Age (years) | diagnosis (weeks/months) | control Ag | hsp60 | p277 (V) |
| 1. | LM | 32 | 3.5 months | + | + | − |
| 2. | G | 25 | 24 months | + | + | − |
| 3. | H | 23 | 6 months | + | + | − |
| 4. | DV | 20 | 3 weeks | + | + | − |
| | | | 5 weeks | + | + | + |
| 5. | SD | 15 | 6 weeks | + | + | + |
| 6. | P | 15 | 4 weeks | + | − | − |
| 7. | G | 60* | 5 weeks | + | + | + |
| | | | 7 weeks | + | + | + |
| 8. | F | 45* | 6 weeks | + | + | + |
| 9. | IS | 53 | 2 weeks | + | + | − |
| 10. | T | 20 | 4 weeks | + | + | + |
| 11. | KK | 21 | 4 weeks | + | + | − |
| 12. | RI | 40 | 6 weeks | + | − | − |
| 13. | MS | 5 | 1 week | + | + | − |

TABLE 6-continued

Proliferative T cell response of IDDM patients

| | | | Time since | T-cell responses (stimulation index) to: | | |
|---|---|---|---|---|---|---|
| Patient | | Age (years) | diagnosis (weeks/months) | control Ag | hsp60 | p277 (V) |
| 14. | KB | 5 | 2 months | + | + | + |
| 15. | BI | 11.3 | 3 weeks | + | − | − |
| 16. | YY | 60 | 2 months | + | + | − |
| 17. | KA | 12 | 4 weeks | − | − | − |
| 18. | ZA | 12 | 4 weeks | + | + | + |
| 19. | A | 17.5 | 11.5 years | + | + | + |
| 20. | N | 17.5 | 7.5 years | + | + | + |
| 21. | A | 19.7 | 5.7 years | + | + | + |

*Patients positive for anti-GAD antibodies, are type I and not type II diabetics despite advanced age of onset.

TABLE 7

Proliferative T cell response of healthy blood donors

| | T-cell responses (stimulation index) to: | | |
|---|---|---|---|
| Donor | control Ag | hsp60 | p277 (V) |
| 1 | + | − | − |
| 2 | + | − | − |
| 3 | + | nd | + |
| 4 | + | − | − |
| 5 | + | + | + |
| 6 | + | − | − |
| 7 | + | − | − |
| 8 | + | − | − |
| 9 | + | − | − |
| 10 | + | − | − |
| 11 | + | + | − |
| 12 | + | − | − |
| 13 | + | + | − |
| 14 | + | − | − | nd: not done

Table 8 is a summary table showing that 86% and 52%C) of the patients responded to hsp60 and to p277(V) compared to 21% and 14% of the controls (p<0.05). Thus, the IDDM group was significantly positive for T cell responses to hsp60 and p277(V). This leads to the conclusion that the incidence of hsp60 and p277(V) reactive individuals is higher among IDDM patients than among healthy people.

TABLE 8

Incidence of positive T-cell rest responsiveness in IDDM and healthy individuals:

| | Incidence of T-cell responses to (%) | |
|---|---|---|
| Responders | hsp60 | p277 (V) |
| IDDM | 18/21 (86) | 11/21 (52)* |
| Healthy | 3/14 (21) | 2/14 (14) |

*p < 0.05 by $x^2$ analysis, compared to the incidence of anti-p277 (V) responders in healthy blood donors.

EXAMPLE 9

NOD T-cell -proliferation to p277(Lys$^{19}$)

Figure 3:
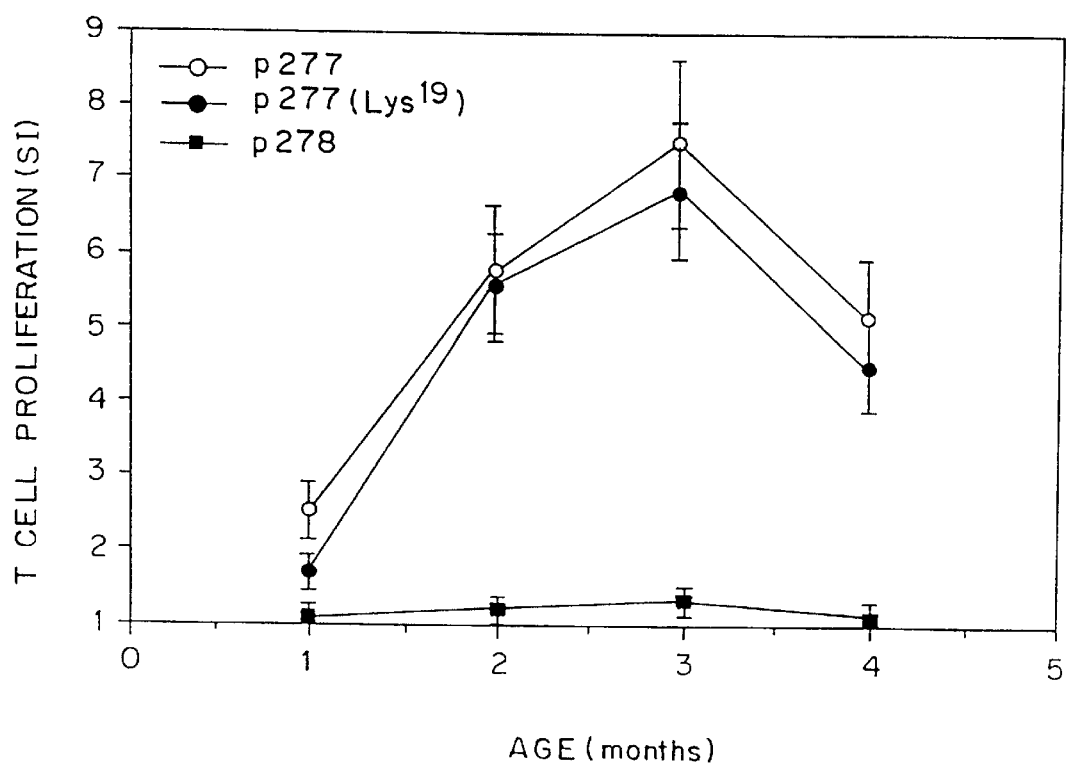
FIG. 3 shows that NOD spleen T cells proliferate in the presence of the peptide p277(Lys$^{19}$). The spleens of 5 female NOD mice were tested in each age group for T cell proliferation in response to the peptides p277(Lys$^{19}$) (closed circles), p277 (open circles) and control peptide p278 (closed squares).

The p277(Lys$^{19}$) peptide differs from p277 by one amino-acid. In order to confirm that p277(Lys$^{19}$) is an autoantigen in NOD IDDM, we compared T-cell proliferation to peptide p277 and to peptide p277(Lys$^{19}$). FIG. 3 demonstrates that T cells of female NOD spleens proliferated to the p277 (Lys$^{19}$) peptide to the same extent as to p277. There was no response to the control peptide p278.

Figure 4:
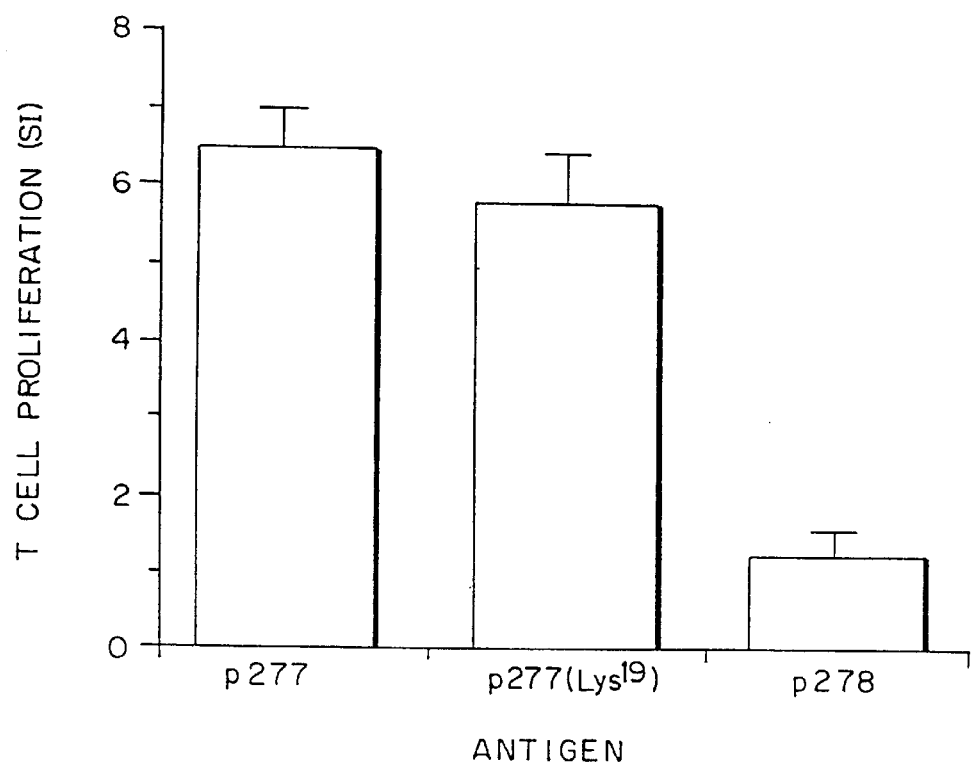
FIG. 4 shows that NOD T cells of the diabetogenic clone C9 proliferate in response to the peptide p277(Lys$^{19}$).

The above results were confirmed using clone C9, a diabetogenic NOD T-cell clone that was found to respond to the human peptide p277 (Elias et al., 1991). C9 cells were found to proliferate to the p277(Lys$^{19}$) peptide to the same extent as to the p277 peptide (FIG. 4).

EXAMPLE 10
Treatment of NOD female mice with p277(Lys$^{19}$)

The present inventors have previously reported that advanced insulitis present in 3 month old female NOD mice could be arrested by treating the mice with a single injection of human p277; the treated mice developed a lower incidence of clinically overt diabetes and death from severe hyperglycemia. To test whether the peptide p277(Lys$^{19}$), that is the self mouse p277 peptide, was also effective, we treated 3 month old female NOD mice with 100 μg of either human p277 or p277(Lys$^{19}$) in IFA.

Peptides p277 or p277(Lys$^{19}$) at a concentration of 2 mg/ml in phosphate buffered saline (PBS) were emulsified with an equal volume of incomplete Freund's adjuvant (IFA). Groups of 10 female 3-month old NOD mice were injected subcutaneously with 0–1 ml (100 μg peptide) of emulsion containing either peptide. Control mice were injected with an emulsion of PBS and IFA. Mice were bled every 4 weeks and blood glucose levels were determined with Beckmann Glucose Analyser II. The incidence of hyperglycemia and death from diabetes was scored at 6 months of age. Mice were considered diabetic if their blood glucose was greater than 11 mmol/L.

The results are shown in Table 9. At 6 months of age, 90% of the control mice were overtly hyperglycemic and 60% had died of diabetes. In contrast, treatment with either p277 or p277(Lys$^{19}$) prevented both diabetes (40% and 50% incidence, respectively) and death (10% and 20% incidence, respectively). Thus, the mouse self peptide p277(Lys$^{19}$) seems to be as effective as the foreign p277 in the therapy of advanced insulitis.

TABLE 9

Treatment of Diabetes with p277 or p277 (Lys$^{19}$)

| Treatment at 3 months | Diabetes at 6 months | |
|---|---|---|
| | Hyperglycemia (%) | Mortality (%) |
| p277 (Lys$^{19}$) | 50* | 20* |
| p277 | 40* | 10* |
| PBS | 90* | 60 |

*p < 0.05

These results show that the proliferative responses of NOD T cells detected using the human hsp60 molecule and its p277 peptide are the equivalent of an autoimmune response to mouse hsp60 and to the mouse p277(Lys$^{19}$) sequence. This was demonstrated for the diabetogenic C9 T cell clone as well as for the spontaneous response developing in the spleens of prediabetic mice. Moreover, p277 (Lys$^{19}$) was as effective as p277 in the treatment of diabetes in NOD mice. Spleen T cells of age and sex matched mice of other strains did not manifest a spontaneous T-cell proliferative response to p277 (not shown).

The finding of autoimmunity to a mouse hsp60 sequence targeted by diabetogenic T cells supports the general belief that IDDM is caused by an autoimmune process.

EXAMPLE 11
Treatment of STZ-induced diabetes by p277(V)

Streptozotocin (STZ) is a beta-cell specific toxin which can cause toxic diabetes by destroying the beta-cells within 24–48 h if one dose of 200 mg/kg is injected. Given in small subtoxic doses it induces in genetically susceptible mice insulitis leading to diabetes. The inflammatory process can take 20–30 days, depending on the dose of STZ. The regular protocol for STZ-induced diabetes is a dose of 200 mg STZ per kg body weight, given in 5 equal doses of 40 mg/kg on consecutive days (Like and Rossini, 1976) and the model is called low-dose STZ. We found that if the total dose is reduced to 150 mg/kg (30 mg/Kg×5), diabetes develops within 80–100 days. This slowly progressing form of STZ-induced diabetes probably better resembles the autoimmune diabetes in humans and is of the same duration as the preclinical stage of the spontaneous diabetes in NOD mice (Castano and Eisenbarth, 1990). Moreover, the acute toxic effects are diminished as the dose is reduced.

The 60 kDa heat shock protein (hsp60) plays a role in both NOD (Elias et al., 1990) and STZ-induced (Elias et al., 1994) diabetes. We have previously shown that both antibody and T cell proliferative responses to hsp60 occur before the onset of overt diabetes. T cell clones specific to hsp60 were derived from prediabetic NOD mice and could adoptively transfer insulitis and hyperglycemia in young NOD (Elias et al., 1991)) or τγ∠δ NOD mice. The NOD diabetogenic T cell clones recognize a 24 amino acid long peptide of the hsp60 sequence 437–460 we call p277. STZ-induced diabetes is also accompanied by anti-p277 T cell responses at the preclinical stage.

Previous examples have shown that the p277(Val$^6$-Val$^{11}$) peptide protects NOD mice. The present experiment tests the efficacy of p277(V) treatment in the low dose STZ model.

Figure 5:
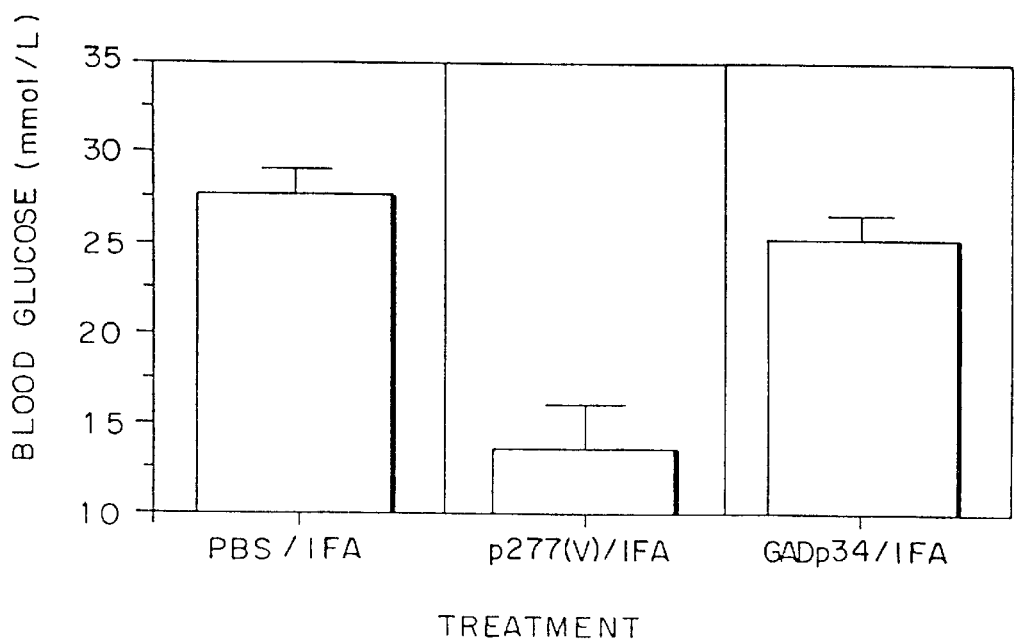
FIG. 5 is a graph showing the effectiveness of pretreatment with p277(V) in IFA in the prevention of STZ-induced diabetes as compared to control treatment or treatment with GADp34.

Male mice, 10 per group, were treated with a dose of STZ 30 mg/kg, daily for 5 days. One week later, the mice were treated with 100 μg of either p277(V) in oil, a peptide of glutamic acid decarboxylase (GADp34) described by Kaufman et al, 1993, as being involved in the diabetes of NOD mice, or oil alone. The treatment was repeated on day 85. On day 100, the mice were bled and their blood tested for hyperglycemia (glucose concentration greater than 15 nmol/L). The results are summarized in FIG. 5. It can be seen that the mean blood glucose of the groups of mice treated with GADp34 or untreated were in the hyperglycemic range. In contrast, the mean blood glucose of the mice treated with p277(V) was in the normal range. Thus, p277(V) can be effective in treating diabetes induced in male C57BL/ksj mice by STZ as well as the spontaneous diabetes developing in the genetically disparate female NOD mice. The applicability of p277(V) therapy is not limited to diabetes of only one cause or to only one genotype or gender.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional method steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Bendelac A, Carnaud C, Boitard C, Bach J F. (1987) Syngeneic transfer of autoimmune diabetes from diabetic NOD ice to healthy neonates. Requirement for both L3T4+ and Ly+–2+T cells. *J Exp Med,* 166:823–32.

Bowman M A, Leit er E H and Atkinson M A. (1994) Prevention of diabetes in the NOD mouse: implications for therapeutic intervention in human disease. *Immunology Today,* 15:115–20.

Castano L, Eisenbarth G S. (1990) Type-I diabetes: a chronic autoiohune disease of human, mouse, and rat. *Annu Rem Immunol,* 8:647–79.

Elias, Dana. (1994) The NOD mouse: A model for autoimmune insulin-dependent diabetes. *Autoimmune Disease models, A Guidebook,* pp 147–61.

Elias D, Markovits D, Reshef T, van-Der Zee R and Cohen IR (1990) Induction and therapy of autoimmune diabetes in the non-obese diabetic (NOD/Lt) mouse by a 65-kDa heat shock protein. *Proc Nati Acad Sci USA,* 87:1576–80.

Elias D, Prigozin H, Polak N, Rapoport N, Lohse A W, Cohen IR (1994) Autoimmune diabetes induced by the β-cell toxin streptozotocin. *Diabetes,* 43:992–98.

Elias D, Reshef T, Birk O S, van der Zee R, Walker M D, Cohen I R. (1991) Vaccination against autoimmune mouse diabetes with a T-cell epitope of the human 65 kDa heat shock protein. *Proc Nati Acad Sci USA,* 88:3088–91.

Elias D. and Cohen I R. (1994) Peptide therapy for diabetes in NOD mice. *The Lancet,* 343:704–06.

Kaufman DL, Clare-Salzler M, Tian J, Forsthuber T. Ting G S P, Robinson P, Atkinson M A, Sercarz E E, Tobin A J, Lehmann PV. (1993) Spontaneous loss of T-cell tolerance to glutamic acid decarboxylase in murine insulin-dependent diabetes. *Nature,* 366:69–72.

Like A A, Rossini A A (1976) Streptozotocin-induced pancreatic insulitis: new model of diabetes mellitus. *Science,* 193:415–17.

Mosmann T. R. and Coffman R. I. (1989) *Ann Rev Immunol,* 7:145–73.

Tisch R, Yang X D, Singer S M, Liblav R S, Fuggar L, McDevitt H O. (1993) Immune response to glutamic acid decarboxylase correlates with insulitis in non-obese diabetic mice. *Nature,* 366:72–75.

What is claimed is:

1. A peptide of the sequence I:

$$\text{Val-Leu-Gly-Gly-Gly-}X_1\text{-Ala-Leu-Arg-}X_2\text{-} \quad\quad (I)$$
$$\text{Ile-Pro-Ala-Leu-Asp-Ser-Leu-}X_3\text{-Pro-Ala-Asn-}$$
$$\text{Glu-Asp (SEQ ID NO:6 or 8)}$$

wherein $X_1$ is a Cys or Val residue, $X_2$ is a Val residue, and $X_3$ is a Thr or Lys residue, and salts and functional derivatives thereof prepared from the functional groups which occur as side chains on the residues thereof or the N- or C-terminal groups thereof.

2. A peptide according to claim 1 herein designated p277(Val$^{11}$) wherein $X_1$ is Cys, $X_2$ is Val and $X_3$ is Thr.

3. A peptide according to claim 1 herein designated p277(Val$^6$-Val$^{11}$) wherein both $X_1$ and $X_2$ are Val and $X_3$ is Thr.

4. A peptide according to claim 1 herein designated p277(Val$^{11}$-Lys$^{19}$) wherein $X_1$ is Cys, $X_2$ is Val and $X_3$ is Lys.

5. A peptide according to claim 1 herein designated p277(Val$^{6,11}$-Lys$^{19}$) wherein both $X_1$ and $X_2$ are Val and $X_3$ is Lys.

6. A method for diagnosing the presence or incipience of IDDM in a patient, comprising testing the blood or urine of said patient with a peptide according to of claim 1 as antigen for the presence of antibodies or T cells which are immunologically reactive with human hsp60.

7. A method according to claim 6 comprising testing said patient for the presence of anti-hsp60 antibodies or of a T cell which immunoreacts with hsp60, whereby a result indicating the positive presence of anti-hsp60 antibodies or of a T cell which immunoreacts with hsp60 indicates a high probability of the presence or incipience of IDDM.

8. A method according to claim 6, wherein said patient is tested for the presence of anti-hsp60 antibodies.

9. A method according to claim 8, wherein the test method comprises a radioimmunoassay.

10. A method according to claim 9, wherein the test method comprises an ELISA test.

11. A kit for diagnosing the presence of IDDM by testing for the presence of anti-hsp60 antibodies, according to the method of claim 6, comprising:

(i) an antigen being the peptide of claim 1; and (ii) a tagged antibody capable of recognizing the non-variable region of said anti-hsp60 antibodies to be detected.

12. A kit according to claim 11, wherein said antigen is immobilized on a solid phase.

13. A kit according to claim 11, further including instructions for use of the kit in the diagnosis of IDDM.

14. A kit according to claim 11, wherein the tag is selected from the group consisting of radioisotopes, enzymes, chromophores and fluorophores.

15. A method according to claim 6, wherein said patient is tested for the presence of a T cell which immunoreacts with hsp60.

16. A method according to claim 15, wherein the test;
method comprises a T cell proliferation test comprising the following steps:

(i) preparing a mononuclear cell fraction containing T cells from a blood sample obtained from said patient;

(ii) adding to said mononuclear cell fraction an antigen selected from a peptide of claim 1;

(iii) incubating said cell fraction in the presence of said antigen for a suitable period of time and under suitable culture conditions;

(iv) adding a labeled nucleotide to the incubated cell culture of (iii) at a suitable time before the end of said incubation period to provide for the incorporation of said labeled nucleotide into the DNA of proliferating T cells;

and (v) determining the amount of proliferating T cells by analysis of the amount of labeled nucleotide incorporated into said T cells.

17. A method according to claim 15, wherein the test method comprises a T cell cytokine response test comprising the following steps:

(i) preparing a mononuclear cell fraction containing T cells from a blood sample obtained from said patient;

(ii) adding to said mononuclear cell fraction an antigen selected from a peptide of claim 1;

(iii) incubating said cell fraction in the presence of said antigen for a suitable period of time and under suitable culture conditions; and (iv) measuring the presence of cytokine secreted by the responding lymphocytes into the medium.

18. A method according to claim 17, wherein the cytokine is IFN-γ, IL-2, IL-4, IL-6, IL-10, TNF-α or TGFβ.

19. A kit for diagnosing the presence of IDDM by testing for the presence of a T cell which immunoreacts with hsp60 according to the method of claims 6, comprising:
   (i) an antigen being a peptide of claim 1;
   (ii) a labeled nucleotide; and
   (iii) a suitable medium for culture of lymphocytes.

20. A kit for diagnosing the presence of IDDM by testing for the presence of a T cell which immunoreacts with hsp60 according to the method of claim 6, comprising:
   (i) an antigen being a peptide of claim 1;
   (ii) a suitable medium for culture of lymphocytes; and
   (iii) an assay kit for measuring the presence of the cytokine secreted by the responding lymphocytes into the medium.

21. A kit according to claim 19, further including instructions for use of the kit in the diagnosis of IDDM.

22. A method according to claim 15, wherein said antigen selected from a peptide of claim 1 is injected subcutaneously into a patient and the occurrence of a detectable skin reaction is observed.

23. A pharmaceutical composition comprising a peptide of claim 1 and a pharmaceutically acceptable carrier.

24. A pharmaceutical composition according to claim 23 for the prevention or treatment of IDDM.

25. A method for the prevention or treatment of IDDM, comprising administering to a human subject an effective amount of a peptide of claim 1 in an appropriate carrier.

26. A pharmaceutical composition according to claim 23, wherein said peptide is the peptide of claim 1 selected from the group consisting of the peptides herein designated p277 (Val$^{11}$) wherein $X_1$ is Cys, $X_2$ is Val and $X_3$ is Thr; p277 (Val$^6$-Val$^{11}$) wherein both $X_1$ and $X_2$ are Val and $X_3$ is Thr; p277 (Val$^{11}$-Lys$^{19}$) wherein $X_1$ is Cys, $X_2$ is Val and $X_3$ is Lys; p277 (Val$^{6, 11}$-Lys$^{19}$) wherein both $X_1$ and $X_2$ are Val and $X_3$ is Lys, and salts and functional derivatives thereof prepared from the functional groups which occur as side chains on the residues thereof or the N- or C-terminal groups thereof.

* * * * *

UNITED STATES PATENT AND TRADEMARK OFFICE
CERTIFICATE OF CORRECTION

PATENT NO. : 6,180,103 B1
DATED : January 30, 2001
INVENTOR(S) : Cohen et al

Page 1 of 1

It is certified that error appears in the above-identified patent and that said Letters Patent is hereby corrected as shown below:

Column 1,
Line 28, delete "Val–Leu–Gly–Gly–Gly–$X_1$–Ala–Leu—Arg–$X_2$–" and insert therefor -- Val–Leu–Gly–Gly–Gly–$X_1$–Ala–Leu–Leu—Arg– $X_2$- --.

Signed and Sealed this

Seventh Day of August, 2001

*Attest:*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO. : 6,180,103 B1  Page 1 of 1
DATED : January 30, 2001
INVENTOR(S) : Cohen et al.

It is certified that error appears in the above-identified patent and that said Letters Patent is hereby corrected as shown below:

Column 21,
Line 28, delete "Val-Leu-Gly-Gly-Gly- $X_1$-Ala-Leu-Arg- $X_2$-" and insert therefor
-- Val-Leu-Gly-Gly-Gly- $X_1$-Ala-Leu-Leu-Arg- $X_2$- --

Signed and Sealed this

Seventeenth Day of September, 2002

Attest:

JAMES E. ROGAN
Attesting Officer  *Director of the United States Patent and Trademark Office*

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 24 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 1:

Val Leu Gly Gly Gly Cys Ala Leu Leu Arg Cys Ile Pro Ala Leu Asp
1               5                   10                  15

Ser Leu Thr Pro Ala Asn Glu Asp
            20

(2) INFORMATION FOR SEQ ID NO: 2:

(i) SEQUENCE CHARACTERISTICS:
      (A) LENGTH: 24 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Peptide
      (B) LOCATION:6, 11, 19

```
            (D) OTHER INFORMATION:/note= "Xaa at pos. 6/11 = Cys or
                Val; Xaa at pos. 19 = Thr or Lys; wherein Xaa at pos.
                6/11 are not both Cys when Xaa at pos. 19 is Thr."

(xi) SEQUENCE DESCRIPTION: SEQ ID NO: 2:

Val Leu Gly Gly Gly Xaa Ala Leu Leu Arg Xaa Ile Pro Ala Leu Asp
1               5                   10                  15

Ser Leu Xaa Pro Ala Asn Glu Asp
            20

(2) INFORMATION FOR SEQ ID NO: 3:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

Val Leu Gly Gly Gly Cys Ala Leu Leu Arg Cys Ile Pro Ala Leu Asp
1               5                   10                  15

Ser Leu Lys Pro Ala Asn Glu Asp
            20

(2) INFORMATION FOR SEQ ID NO: 4:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:19
        (D) OTHER INFORMATION:/note= "Xaa at position 19 is Thr
            or Lys"

(xi) SEQUENCE DESCRIPTION: SEQ ID NO: 4:

Val Leu Gly Gly Gly Val Ala Leu Leu Arg Cys Ile Pro Ala Leu Asp
1               5                   10                  15

Ser Leu Xaa Pro Ala Asn Glu Asp
            20

(2) INFORMATION FOR SEQ ID NO: 5:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

Val Leu Gly Gly Gly Val Ala Leu Leu Arg Cys Ile Pro Ala Leu Asp
1               5                   10                  15

Ser Leu Lys Pro Ala Asn Glu Asp
            20

(2) INFORMATION FOR SEQ ID NO: 6:

(i) SEQUENCE CHARACTERISTICS:
```

(A) LENGTH: 24 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION:19
(D) OTHER INFORMATION:/note= "Xaa at position 19 is Thr
or Lys"

(xi) SEQUENCE DESCRIPTION: SEQ ID NO: 6:

Val Leu Gly Gly Gly Cys Ala Leu Leu Arg Val Ile Pro Ala Leu Asp
1               5                   10                  15

Ser Leu Xaa Pro Ala Asn Glu Asp
            20

(2) INFORMATION FOR SEQ ID NO: 7:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 7:

Val Leu Gly Gly Gly Cys Ala Leu Leu Arg Val Ile Pro Ala Leu Asp
1               5                   10                  15

Ser Leu Lys Pro Ala Asn Glu Asp
            20

(2) INFORMATION FOR SEQ ID NO: 8:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:19
        (D) OTHER INFORMATION:/note= "Xaa at position 19 is Thr
            or Lys"

(xi) SEQUENCE DESCRIPTION: SEQ ID NO: 8:

Val Leu Gly Gly Gly Val Ala Leu Leu Arg Val Ile Pro Ala Leu Asp
1               5                   10                  15

Ser Leu Xaa Pro Ala Asn Glu Asp
            20

(2) INFORMATION FOR SEQ ID NO: 9:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 9:

Val Leu Gly Gly Gly Val Ala Leu Leu Arg Val Ile Pro Ala Leu Asp

-continued

```
1               5                10               15
Ser Leu Lys Pro Ala Asn Glu Asp
            20
```

(2) INFORMATION FOR SEQ ID NO: 10:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

```
Asn Glu Asp Gln Lys Ile Gly Ile Glu Ile Ile Lys Arg Thr Leu Lys
1               5                10               15
Ile
```